US012023160B1

(12) United States Patent
Cuestas Rodríguez

(10) Patent No.: US 12,023,160 B1
(45) Date of Patent: Jul. 2, 2024

(54) NON-INVASIVE REMOTE SYSTEM AND METHOD TO DETERMINE THE PROBABILITY OF DECEIT BASED ON ARTIFICIAL INTELLIGENCE

(71) Applicant: Carlos Andrés Cuestas Rodríguez, Bogota (CO)

(72) Inventor: Carlos Andrés Cuestas Rodríguez, Bogota (CO)

( * ) Notice: Subject to any disclaimer, the term of this patent is extended or adjusted under 35 U.S.C. 154(b) by 0 days.

(21) Appl. No.: 18/474,931

(22) Filed: Sep. 26, 2023

Related U.S. Application Data

(63) Continuation of application No. PCT/IB2023/057468, filed on Jul. 21, 2023.

(30) Foreign Application Priority Data

Jun. 16, 2023 (CO) .......................... NC2023/0007913

(51) Int. Cl.
*A61B 5/16* (2006.01)
*A61B 5/00* (2006.01)
(Continued)

(52) U.S. Cl.
CPC ............ *A61B 5/164* (2013.01); *A61B 5/0205* (2013.01); *A61B 5/1103* (2013.01); *A61B 5/7225* (2013.01); *A61B 5/7264* (2013.01); *G06V 40/161* (2022.01); *G06V 40/171* (2022.01); *G06V 40/172* (2022.01); *G06V 40/176* (2022.01); *G06V 40/193* (2022.01); *G06V 40/70* (2022.01); *A61B 5/02405* (2013.01); *A61B 5/02416* (2013.01); *A61B 2562/0204* (2013.01)

(58) Field of Classification Search
CPC ..... A61B 5/164; A61B 5/0205; A61B 5/1103; A61B 5/7225; A61B 5/7264; A61B 5/02405; A61B 5/02416; A61B 2562/0204; G06V 40/161; G06V 40/171; G06V 40/172; G06V 40/176; G06V 40/193; G06V 40/70
See application file for complete search history.

(56) References Cited

U.S. PATENT DOCUMENTS 6,375,623 B1 * 4/2002 Gavriely ............... A61B 5/1135
 600/595
9,814,400 B1 * 11/2017 Cendrillon ........... A61B 5/7221
(Continued)

FOREIGN PATENT DOCUMENTS

EP  2960862 A1  12/2015

*Primary Examiner* — Wesley J Tucker
(74) *Attorney, Agent, or Firm* — The Morales Law Firm; Joseph L. Morales

(57) ABSTRACT

Non-invasive system and method to determine a probability of deceit based on the remote measurement of physiological changes that the evaluated individual presents when interacting with stimuli provided by the system after a pre-interview assisted by an avatar. The system comprises an interaction module, a face recognition and localization module, a processing module, and a deceit probability determination module. The system records the conscious responses of the evaluated individual and determines the physiological variables of the individual, and their changes caused by stress and cognitive load in response to the stimuli generated to calculate a probability of deceit in the conscious responses made by the individual.

13 Claims, 3 Drawing Sheets

(51) Int. Cl.
*A61B 5/0205* (2006.01)
*A61B 5/024* (2006.01)
*A61B 5/11* (2006.01)
*G06V 40/16* (2022.01)
*G06V 40/18* (2022.01)
*G06V 40/70* (2022.01)

(56) References Cited

U.S. PATENT DOCUMENTS

| | | | | |
|---|---|---|---|---|
| 10,325,144 | B2 * | 6/2019 | Zhang | G06F 1/163 |
| 10,565,763 | B2 * | 2/2020 | Wang | G06V 40/172 |
| 10,693,872 | B1 * | 6/2020 | Larson | H04L 63/0861 |
| 11,194,997 | B1 * | 12/2021 | Zhang | G06T 3/0006 |
| 11,461,952 | B1 * | 10/2022 | Bosnak | G06V 20/20 |
| 11,837,338 | B2 * | 12/2023 | Orbach | G16H 10/20 |
| 2003/0016726 | A1 * | 1/2003 | Pavlidis | A61B 5/164 |
| | | | | 374/45 |
| 2006/0116555 | A1 * | 6/2006 | Pavlidis | A61B 5/6888 |
| | | | | 600/300 |
| 2007/0100216 | A1 | 5/2007 | Radcliffe et al. | |
| 2013/0139259 | A1 * | 5/2013 | Tegreene | H04N 21/44218 |
| | | | | 726/22 |
| 2014/0276104 | A1 | 9/2014 | Tao et al. | |
| 2016/0098592 | A1 * | 4/2016 | Lee | G06F 18/24155 |
| | | | | 434/236 |
| 2017/0367590 | A1 * | 12/2017 | Sebe | G06T 7/90 |
| 2020/0251190 | A1 * | 8/2020 | Glasner | A61B 5/7257 |
| 2020/0320770 | A1 * | 10/2020 | Charlson | G06Q 50/26 |
| 2020/0367810 | A1 * | 11/2020 | Shouldice | A61B 5/681 |
| 2020/0383621 | A1 * | 12/2020 | Cuestas Rodriguez | A61B 5/11 |
| 2021/0067692 | A1 * | 3/2021 | Dimpas | G06V 40/165 |
| 2021/0125149 | A1 * | 4/2021 | Yu | G06V 40/20 |
| 2022/0245594 | A1 * | 8/2022 | Baid | G06F 21/6245 |
| 2022/0328070 | A1 * | 10/2022 | Chang | G11B 27/036 |
| 2023/0147868 | A1 * | 5/2023 | Mattavelli | B63C 11/12 |
| | | | | 2/9 |
| 2023/0274582 | A1 * | 8/2023 | Vance | G06V 40/70 |
| | | | | 382/116 |
| 2023/0309882 | A1 * | 10/2023 | Ye | A61B 5/015 |
| | | | | 600/301 |
| 2023/0360772 | A1 * | 11/2023 | Manteau-Rao | G16H 40/67 |
| 2023/0363654 | A1 * | 11/2023 | Gollakota | A61B 5/02405 |

* cited by examiner

NON-INVASIVE REMOTE SYSTEM AND METHOD TO DETERMINE THE PROBABILITY OF DECEIT BASED ON ARTIFICIAL INTELLIGENCE

CROSS-REFERENCE TO RELATED APPLICATIONS

The present application is a continuation of, and claims priority from, International Application PCT/IB2023/057468 filed on Jul. 21, 2023, and Colombian application NC2023/0007913 filed on Jun. 16, 2023, which applications are incorporated herein by reference in their entireties.

FIELD OF THE INVENTION

The present invention is associated to systems and methods to estimate the probability of deceit from an individual, based on the variation of physiological signals caused by cognitive load and stress derived from deceit.

BACKGROUND OF THE INVENTION

Deception proof systems are widely used in security procedures by government entities, military, or private companies. The objective of the systems is to verify if the evaluated individual is answering in a deceitful or honest way to questions that are asked.

Most deceit detection methodologies have focused on the physical measurement of physiological reactions derived from activation of the ANS (Autonomic Nervous System). Numerous studies are based on the polygraph, which is typically composed of cardiac activity sensors, electrodermal change sensors, and respiratory pattern sensors.

Other technologies use specialized sensors, such as infrared sensors to detect thermal changes in the skin, or changes in the estimated percentage diameters of the pupils, changes in brain electrical patterns (EEGs), or even a combination of all of the above.

However, there are situations in which the individual cannot be evaluated physically, but the interaction is conducted remotely, such is the case of personnel recruitment processes, insurance claim processes and/or negotiation processes in general, amongst others. In these situations, it is necessary to detect the possibility of deceit by the individual in order to avoid unfavorable negotiations, an inadequate insurance claim, or the incorporation of people who do not meet the expectations of the entities or companies.

However, there are no deceit detectors in the art that can work remotely, since all existing systems have the premise of working in physical contact to obtain physiological signals with the evaluated individual or with a reasonable distance from him/her, always personally, due to the complexity of the signals to be analyzed and the way of obtaining these signals.

Therefore, there is a need in the technique for a remote system that evaluates the changes in a plurality of physiological variables and relates them to responses to stimuli to obtain a calculation of the probability of deceit, without the need for the evaluated individual to be in the same location as the interviewer or the entity requesting the assessment.

BRIEF DESCRIPTION OF THE INVENTION

The present disclosure seeks to provide a non-invasive deceit detection system and method that can also be implemented remotely. In particular, the need to physically connect a series of sensors to the interviewee is eliminated. The system and method revealed here extracts information from the evaluated individual, said information is captured through a device that has a webcam, microphone and/or speaker; and with the information obtained, physiological variables of the evaluated individual are determined, and their changes with respect to different stimuli, to determine the probability of deceit.

The remote deceit detection system according to the present disclosure comprises several modules, including: an interaction module, a face recognition and localization module, a processing module, and a deceit probability determination module.

The system is configured to create an avatar that reflects one or more physical features of the evaluated individual, said avatar is configured to ask questions in the form of an interview to the evaluated individual during an initial stage. In addition, the system is configured to also provide visual, auditory, or combined stimuli different from the avatar.

Additionally, the system is configured to process remote photoplethysmographic signals acquired from sequenced images taken from the face of an evaluated individual, and from the background in front of which said individual is located, in order to extract physiological variables such as the heart rate variability HRV, vasoconstriction, and vasodilation, amongst others. In the acquisition of these signals, the screen in front of which the interviewed individual is located, and the ambient light are used as a light source.

Similarly, image analysis is performed to determine changes in blinking variations and facial expressions produced by stress and cognitive load in response to the stimulus generated by the interaction module. Also, acoustic signals and their changes are processed to infer respiratory patterns and artifacts such as apneas and other. The deceit probability determination module uses the one or more variables obtained, their changes, and the stimuli provided in a machine learning algorithm that delivers as a result the probability of deceit of the conscious responses made by the evaluated individual.

Another aspect of the invention relates to a non-intrusive method of determining the probability of deceit. Said method includes the steps of: a) acquiring images of the individual and the background in which the individual is located; b) locating the face of the individual and identifying physical features of the individual; c) creating an avatar that contains one or more of the physical features of the evaluated individual; d) conducting a pre-interview on general topics using the avatar; e) providing visual, auditory and/or combined stimuli to the evaluated individual; f) locating points of interest on the face of the individual face and on the background; g) obtaining photoplethysmographic signals of the face and changes in lighting of the background where the individual is located; h) processing the signals using filtering strategies; i) compensating the signals for movements of the evaluated individual; j) processing the signals by removing artifacts; k) identifying the blinking of the individual; l) determining physiological variables inferred through an analysis of the photoplethysmographic signals, the acoustic signals, and the images obtained; m) determining changes in physiological variables; and n) calculating the probability of deceit from the changes in the physiological variables and the stimuli provided to the individual using machine learning methods based on artificial intelligence.

DETAILED DESCRIPTION OF THE INVENTION

The present invention provides a non-invasive deceit detection system and method, which can be remotely implemented, eliminating the need to physically connect an array of sensors on the evaluated individual. The system and method revealed here extracts information from the face of the evaluated individual captured through a device that includes a webcam, microphone and/or speaker, and determines facial expressions and physiological variables, and their changes with respect to different stimuli, to determine the probability of deceit.

Among the physiological variables that the system evaluates are variables related to heart rate variability HRV inferred from the color changes produced by light reflection on the person's facial skin, changes in the frequency and duration of blinking, the facial expressions, changes in breathing patterns, and changes in vasoconstriction and vasodilation.

Figure 1:
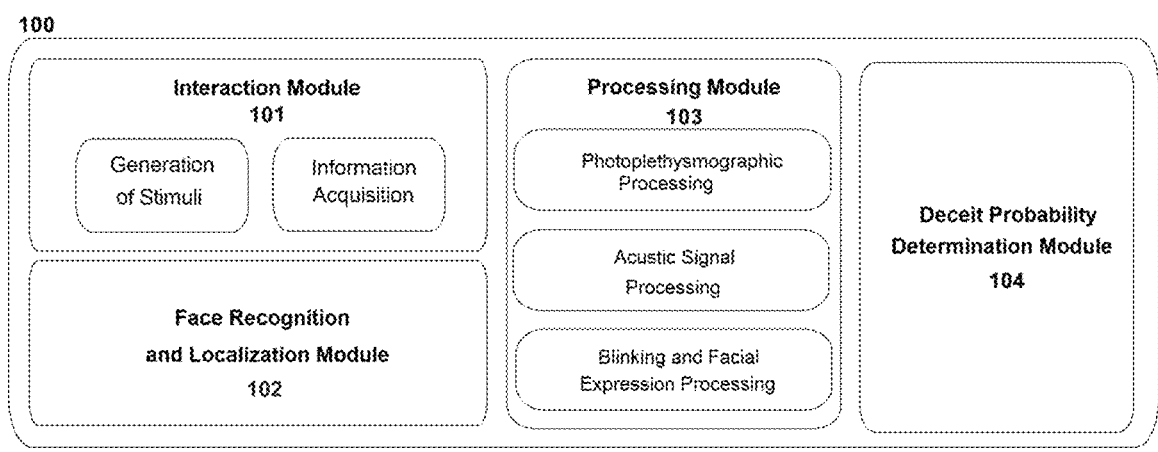
FIG. 1 shows a schematic diagram of the modules of the non-invasive system to detect probability of deceit from the present disclosures.

As shown in FIG. 1, the non-invasive system for detecting the probability of deceit disclosed herein comprises several modules, including: an interaction module (101), a face recognition and localization module (102), a processing module (103), and a deceit probability determination module (104).

Preferably, the system comprises a video camera, a processor, a screen, a microphone, and a sound reproduction device. The interaction module (101) is configured to generate stimuli and to acquire information.

In a preferred modality, the stimuli generated can be visual, auditory, or combined. Additionally, the interaction module is configured to create an avatar that has a humanoid voice and a humanoid appearance, and that adopts one or more physical features of the evaluated individual. The interaction module (101) is also configured to emit a different sound from the stimulus, at a frequency inaudible to a human ear.

In a preferred embodiment of the invention, the screen of the interaction module, together with the ambient light, illuminates the individual and the background in front of which the individual is located during the acquisition of the photoplethysmographic signals. Additionally, the screen is configured to indicate framing guides, which will serve as a guide for the evaluated individual to correctly position the face of the individual in front of the camera. The interaction module (101) also captures information from the microphone channel to be processed later.

Preferably, the light source coming from the screen is configured to implement lighting strategies, that is, it allows lighting changes projected from the screen both in light intensity, modifying what is emitted on the screen in terms of brightness and color spectrum. Most digital cameras include algorithms that change the contrast when capturing video, the calibration system used allows us to infer how the camera adapts to changes in lighting and color at known lighting levels for the processing stage, this also allows us to understand variations amongst various hardware, something that represents an improvement over existing methods.

In a preferred modality of the invention, the camera is configured to take video of the individual, mainly of the face and some points in the background of which the individual is located. The recording sampling frequency is stored between 15 to 30 Hz, typically being stored at 25 Hz, the resolution is at least 640×480 pixels in size within which the framing of the person's face and background will be during the development of the interview.

In the context of the present invention, the processing module (103) comprises three processing units; a remote photoplethysmographic signal processing unit, which is configured to acquire physiological signals such as heart rate variability HRV and changes in vasoconstriction and vasodilation from the photoplethysmographic signals; an acoustic signal processing unit, which is configured to infer respiratory patterns; and an image processing unit, which is configured to determine the frequency and duration of blinking and micro expressions of the face of the evaluated individual. Additionally, the processing module (103) is configured to identify and count the number of people or faces detected in the frame, as well as to identify that the individual coincides with the individual that was initially validated.

In a preferred modality of the invention, the deceit probability determination module (104) is configured to receive as input the data of one or more of the physiological variables obtained from the other modules, changes in said physiological variables, and information on the stimuli, so that it determines the probability of deceit of the conscious responses of the individual.

According to one modality of the invention, the interaction module is configured to emit sound at a frequency inaudible to a human ear during the interview and record the reflected sound, similar to sonar.

Figure 2:
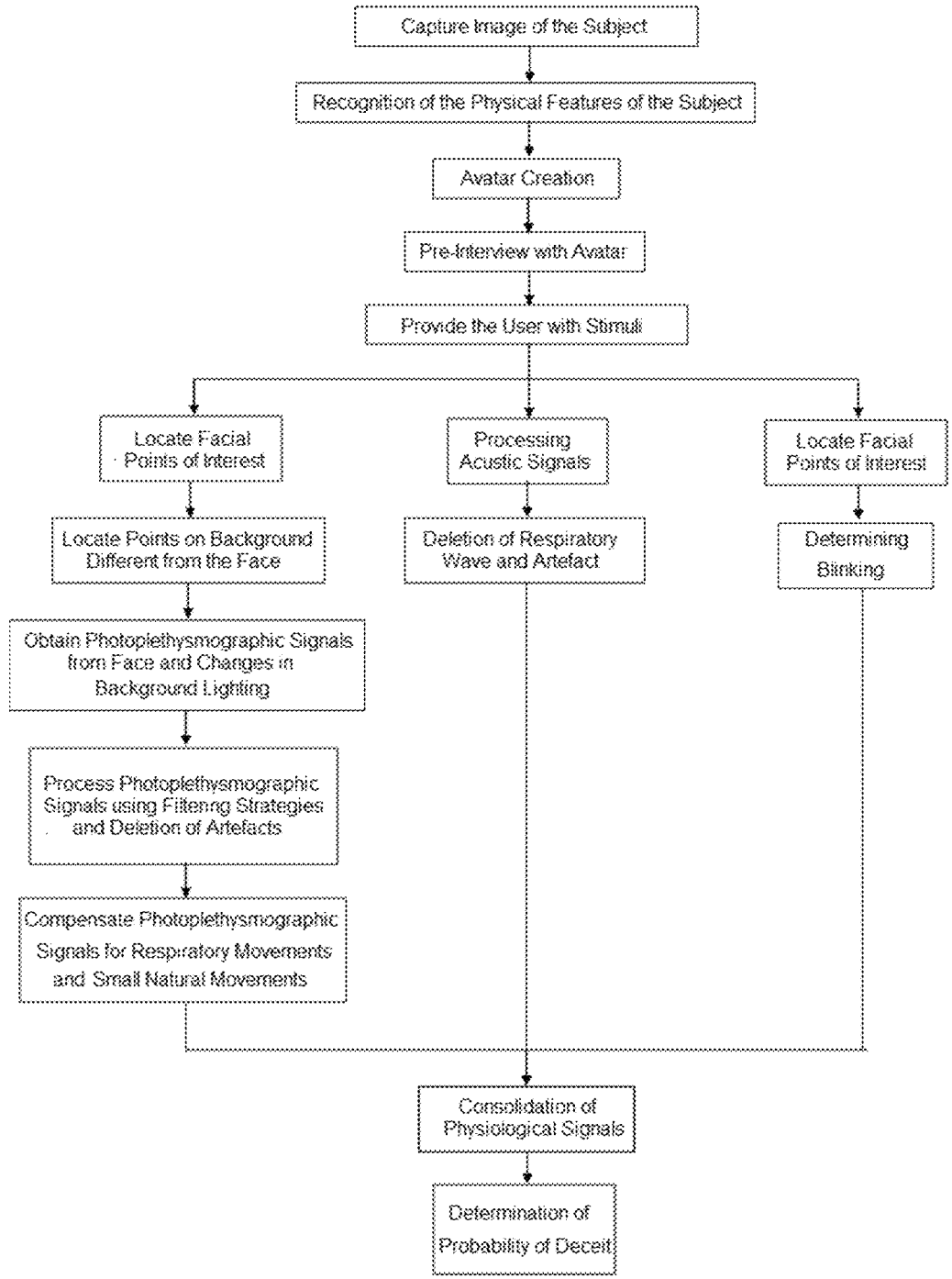
FIG. 2 shows a flow diagram of the non-invasive method of determining the probability of deceit as per the present disclosure.
Figure 3:
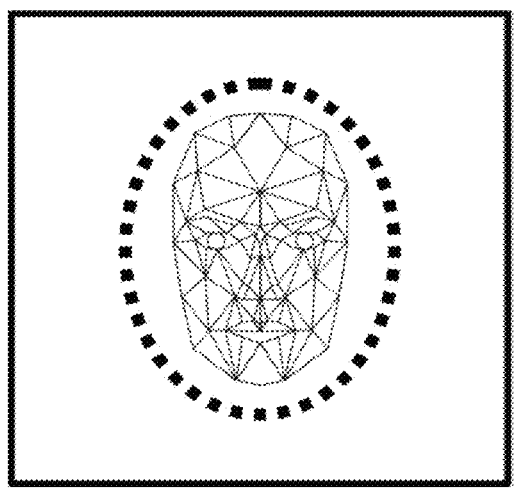
FIG. 3 shows framing guides that the screen displays and that allow the face of the individual to be correctly located within the system and method of the present disclosure.

Another aspect of the invention relates to a non-intrusive method of determining the probability of deceit. FIG. 2 shows a flowchart of said method according to an embodiment of the present invention that includes the steps of: a) acquiring images of the evaluated individual and the background in which it is located; b) locating the face of the individual and identifying physical features of the evaluated individual; c) creating an avatar that contains one or more of the physical features of the evaluated individual; d) conducting a pre-interview on general topics using the avatar; e) providing visual, auditory and/or combined stimuli to the evaluated individual; f) locating points of interest on the face of the individual and on the background; g) obtaining photoplethysmographic signals of the face and changes in lighting of the background where the evaluated individual is located; h) processing the signals using filtering strategies; i) compensating the signals for movements of the evaluated individual; j) processing the signals by removing artifacts; k) identifying the blinking of the evaluated individual; l) determining physiological variables inferred through an analysis of the photoplethysmographic signals, the acoustic signals, and the images obtained; m) determining changes in physiological variables; and n) calculating the probability of deceit from the changes in the physiological variables and the stimuli provided to the evaluated individual using machine learning methods based on artificial intelligence.

In a preferred modality of the invention, the evaluated individual is pre-interviewed, assisted by an avatar that has a humanoid voice and a humanoid appearance and also contains one or more physical features of the evaluated individual. Preferably, in the main interview performed with the individual, the individual is subjected to visual or auditory stimuli or a combination of both.

For the capture of images of the individual, the individual is arranged so that the individual aligns with some framing guides that the screen shows and that allow the face of the individual to be correctly located. The light emitted from the screen has a preponderance of green colors and surrounds the framing guides in order to facilitate the illumination of the face in the spectrum frequency that is analyzed.

Preferably, the images are acquired considering a configuration of colors and an adjustable amount of light given by the screen that is located in front of the individual. The acquired images contain information on both the face of the individual and the background in front of which the individual is located. In this way, information is obtained on changes in ambient lighting.

In the context of the present invention, face localization is implemented by means of computer vision algorithms on a processor. Background tracking techniques ("background subtraction") are used, to differentiate the face of the evaluated individual and the background in front of which the individual is located. This additionally makes it possible to identify whether the changes in light intensity and composition on the face come from physiological changes, or if they are generated by the environment, since, being generated by the environment, the changes would also be reflected in areas other than the face.

In the context of the present invention, the non-intrusive method for determining the probability of deceit analyzes the light reflected from the face of the individual at a frequency compatible with that of their heart activity, identifying variations in the frequencies of light emitted by the screen. and the environment.

According to a modality of the invention, in an initial stage of the method, the evaluated individual is pre-interviewed, assisted by an avatar that has a humanoid voice and a humanoid appearance, and shares one or more physical features with the evaluated individual, which provides the individual with tranquility and familiarity, reducing anxiety and stress associated with the situation, and which is not associated with deceit. The pre-interview is performed raising general issues.

At a later stage, the main interview is performed during which visual or auditory stimuli or a combination of both are generated. Additionally, the individual can interact in such a way that he/her can accept, deny, or explain each of the questions presented.

In a preferred modality of the invention, the method further compensates for the photoplethysmographic signals and the acoustic signal for respiratory movements or natural movements of the individual. Likewise, the signals obtained are filtered and their artifacts are removed. The techniques used for filtering and artifact removal are selected from the group of Fast Fourier Transform (TFF), Welch, Kalman Filter, Adaptive Filter, amongst others. similarly, the method revealed here comprises generating a sound during the interview, different from the auditory stimulus, at a frequency inaudible to a human ear and obtaining the reflected acoustic signal, similar to a sonar.

According to the method revealed here, the acoustic signal analyzed corresponds to the reflected acoustic signal of the signal emitted at a frequency inaudible to a human ear, so that the respiratory patterns are inferred.

For the elimination of artifacts whose origin is in ambient lighting, they are eliminated using the principle of concurrence in time between changes in lighting of the background and those of the face, in this way the lighting artifacts of the face with environmental, not physiological, origin and those of the face are differentiated. Additionally, using and comparing the respiratory wave inferred from the acoustic signal with a respiratory pattern inferred from the heart rate variability HRV derived from the photoplethysmographic signals, to identify artifacts such as apneas and others.

Once the clean photoplethysmographic signal is obtained, the cardiac peaks are estimated to analyze those that should be considered in the analysis and those that should be rejected. In this way, the cardiovascular activity of the evaluated individual is obtained, obtaining a cardiac graph. Additionally, information can be obtained on heart rate, heart rate variability HRV, blood pressure, respiration, and an estimate of the relative changes in the level of oxygen in the blood.

In the context of the present invention, facial image processing uses machine vision techniques, with which changes in facial expressions are assessed and the ocular structure is evaluated to analyze the blinking of the individual. Said evaluation comprises monitoring the detected points of the eye and their horizontal variation over time in the blinking movement with a mathematical estimation of relative coordinates.

In a preferred embodiment of the invention, the probability of deceit is calculated from the one or more physiological variables obtained, such as heart rate variability HRV, changes in blink rate and duration, changes in facial expressions, changes in respiratory patterns, changes in vasoconstriction and vasodilation, and response time. The changes in these variables, together with the information of the stimuli presented, are entered into a machine learning algorithm that provides as a result the probability of deceit of the conscious responses of the individual.

The following table presents examples of different combinations of stimuli, and the different changes in physiological variables that are prioritized to determine the probability of deceit:

| STIMULI | | PRIORITIZED VARIABLES |
| --- | --- | --- |
| TYPE 1 | visuals of a text and sound type | Blink frequency and duration, changes in HRV, respiratory changes, sonar changes, vasoconstriction and vasodilation changes, facial point changes (micro-expressions), Response time. |
| TYPE 2 | Images without text or sound | Blink frequency and duration, changes in HRV, respiratory changes, sonar changes, vasoconstriction and vasodilation changes, facial point changes (micro-expressions), Response time. |
| TYPE 4 | sound | Blink frequency and duration, changes in HRV, respiratory changes, sonar changes, vasoconstriction and vasodilation changes, facial point changes (micro-expressions), Response time. |
| TYPE 5 | Image without text | Blink frequency and duration, changes in HRV, respiratory changes, sonar changes, vasoconstriction and vasodilation changes, facial point changes (micro-expressions), Response time. |

The embodiments disclosed herein exemplify the invention, which is not limited to such embodiments, and its scope may include obvious variations and modifications of such embodiments.

What is claimed is:

1. A non-invasive system for detecting a probability of deceit of an individual, comprising:
    a video camera;

a screen;
a microphone;
a sound reproduction device; and
a processor;
wherein the processor is configured to execute the modules:
an interaction module, configured to:
provide visual and auditory stimuli to the individual through the screen and the sound reproduction device,
obtain images that include a face of the individual and a background where the individual is located through the video camera,
obtain photoplethysmographic signals through the video camera,
obtain acoustic signals through the microphone;
where the interaction module is configured to create an avatar that has a humanoid voice, a humanoid appearance and reflects one or more physical features of the evaluated individual;
where said avatar is configured to conduct a pre-interview;
a face recognition and localization module, which is configured to differentiate the face of the individual from the background using the images acquired by the interaction module;
a processing module,
configured to process the acquired photoplethysmographic signals from the video camera, the acoustic signals from the microphone, and the images from the video camera, to filter the photoplethysmographic signals from the video camera and the acoustic signals from the microphone, and to identify physiological variables and changes in said physiological variables in response to the stimuli that the individual receives from the interaction module;
where the physiological variables identified are one or more of heart rate, blink rate and duration, facial expressions, respiratory patterns, vasoconstriction and vasodilatation, and response time; and
a deceit probability determination module that, based on the physiological variables identified, changes in said physiological variables, and information on the stimuli by the other modules, determines the probability of deceit of the conscious responses of the individual using machine learning methods.

2. The system according to claim 1, wherein the interaction module uses a screen as a light source.

3. The system according to claim 1, wherein the interaction module is configured to perform a main interview to the individual, in which the individual can interact by accepting, denying, or explaining the questions.

4. The system according to claim 1, wherein the interaction module is configured to emit a sound at a frequency inaudible to a human ear during the interview and record the reflected sound.

5. The system according to claim 1, wherein the processing module is configured for removing artifacts from the photoplethysmographic signals and acoustic signals.

6. The system according to claim 1, wherein the processing module is configured to count a number of people or faces in a frame, as well as to identify that the individual coincides with the individual that was initially validated.

7. A non-invasive method for determining a probability of deceit of an individual, comprising:
acquiring images of the individual and a background where the individual is located using a video camera;
locating a face of the individual;
identifying the physical features of the individual;
creating an avatar that has a humanoid voice, a humanoid appearance and reflects one or more physical features of the evaluated individual;
conducting a pre-interview assisted by the avatar on general topics;
providing visual, auditory and/or combined stimuli to the individual through a screen and a sound reproduction device;
locating points of interest on the face of the individual and on the background;
obtaining photoplethysmographic signals using a video camera;
obtaining acoustic signals using a microphone;
processing the photoplethysmographic signals, the acoustic signals, and the images filtering the photoplethysmographic signals and the acoustic signals;
compensating the photoplethysmographic signals and the acoustic signals for movements of the individual;
processing the photoplethysmographic signals, the acoustic signals, and the images by removing artifacts;
identifying blinking of the individual;
determining physiological variables through an analysis of the photoplethysmographic signals, the acoustic signals, and the images obtained;
where the physiological variables identified are one or more of heart rate, blink rate and duration, facial expressions, respiratory patterns, vasoconstriction and vasodilatation, and response time;
determining changes in the determined physiological variables; and
calculating the probability of deceit from the changes in the determined physiological variables and the stimuli provided to the individual using machine learning methods.

8. The method of claim 7, wherein framing guides are provided on a screen for the individual to align the face of the individual.

9. The method of claim 7, wherein a screen is configured to adjust colors and amount of light in an environment where the individual is located.

10. The method of claim 7, wherein locating the face of the individual is performed by computer vision algorithms, such as background tracking.

11. The method of claim 7, which also comprises generating a sound during the interview, different from the auditory stimulus, at a frequency inaudible to a human ear and obtaining the reflected acoustic signal.

12. The method of claim 7, which further comprises using and comparing the respiratory wave inferred from the acoustic signal with a respiratory pattern inferred from the heart rate variability HRV derived from the photoplethysmographic signals, to identify artifacts.

13. The method of claim 7, wherein, the blinking of the individual is evaluated by monitoring the detected points of the eye and their horizontal variation over time in the blinking movement with a mathematical estimation of relative coordinates.

* * * * *